United States Patent [19]
Lindquist et al.

[11] Patent Number: 6,040,492
[45] Date of Patent: Mar. 21, 2000

[54] METHOD OF SECURING A LIQUID IMPERVIOUS SHEET TO A WOUND PAD

[75] Inventors: Bengt W. Lindquist, Lerum; Tomas Fabo, Mölnlycke, both of Sweden

[73] Assignee: Molnlycke Health Care AB, Gothenburg, Sweden

[21] Appl. No.: 09/025,455

[22] Filed: Feb. 18, 1998

[30] Foreign Application Priority Data

Feb. 20, 1997 [SE] Sweden .................................. 9700600

[51] Int. Cl.$^7$ ...................................................... A61F 13/00
[52] U.S. Cl. ............................................... 602/41; 602/58
[58] Field of Search .................................... 604/369, 385; 602/41, 48

[56] References Cited

FOREIGN PATENT DOCUMENTS 2191403A 12/1987 United Kingdom .

*Primary Examiner*—John G. Weiss
*Assistant Examiner*—Kelvin Hart
*Attorney, Agent, or Firm*—Young & Thompson

[57] ABSTRACT

A method of fastening a liquid-impervious sheet (7) to a wound pad (5) that is comprised of an elastic, hydrophilic material and that will expand in all directions when absorbing fluid. The pad (5) is stretched to a given extent both longitudinally and transversally in the plane of the pad and a flat liquid-impervious sheet (7) is then applied to the stretched pad and the load acting on the pad is removed. An absorbent dressing that includes an inventive wound pad (13) is also disclosed.

4 Claims, 1 Drawing Sheet

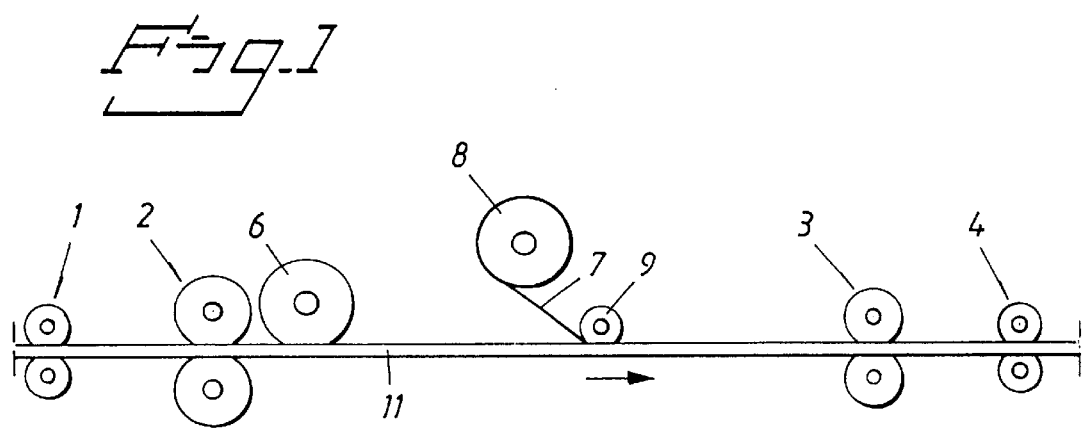
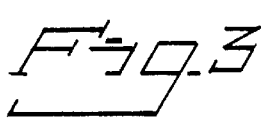
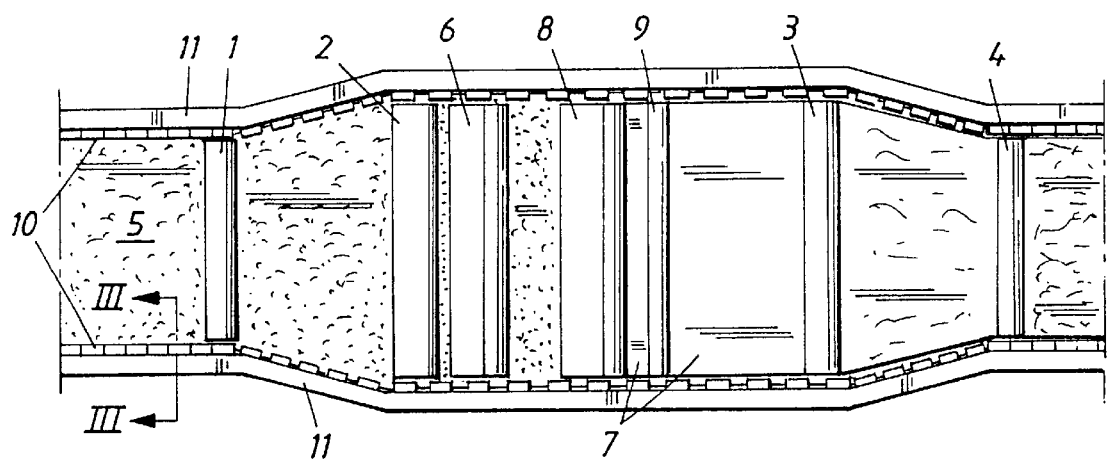
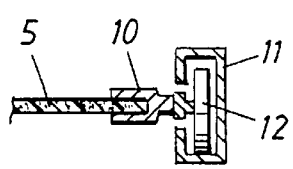
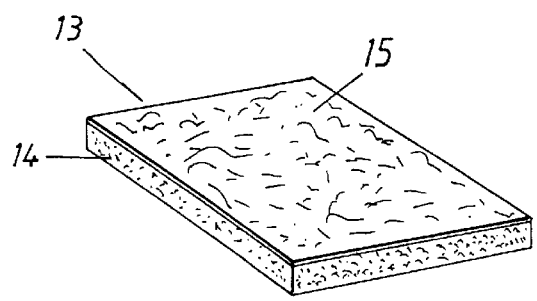

METHOD OF SECURING A LIQUID IMPERVIOUS SHEET TO A WOUND PAD

FIELD OF THE INVENTION

The present invention relates to a method of securing a liquid impervious sheet to a wound pad that is comprised of an elastic, hydrophilic material and that will expand in all directions when absorbing fluid. The invention also relates to a dressing that includes a wound pad to which a liquid-impervious sheet is fastened with the aid of said method.

BACKGROUND OF THE INVENTION

Such a wound pad will often be provided with liquid impervious film, to prevent fluid from seeping from the pad and onto the overlying dressing or onto the wearer's clothing. A wound pad in the form of an hydrophilic foam plate (e.g. polyurethane foam) will endeavour to expand by 30 to 40% in all directions when taking-up fluid, such wound pads often being used in the treatment of traumatic or chronic wounds. Other materials can strive to expand by as much as 100%. Plastic film cannot be made to stretch in keeping with the expansion of the wound pad. Film attached to the upper surface of the wound pad will counteract the expansion of the wound pad, wherewith the wound pad will attempt to arch or curve as the wound pad takes up fluid. There is thus a danger that the ends of such a wound pad applied to a wound will loosen from the wearer's skin, which is, of course, most undesirable.

SUMMARY OF THE INVENTION

A primary object of the present invention is to provide an absorbent wound pad of the aforesaid kind with which the liquid im pervious sheet is able to accompany the expansion of the wound pad as the pad takes up fluid. A secondary object is to increase the flexibility of such a wound pad.

These objects are achieved in accordance with the invention by means of a method of the kind described in the first paragraph, which is characterized by stretching the wound pad to a given extent in the plane of the pad, both longitudinally and laterally, fastening a flat liquid-impervious sheet to the stretched pad, and then removing the load acting on the pad. This results in a three-dimensional liquid-impervious sheet that includes a large number of projections formed by folding or puckering of the sheet as the pad retracts from its stretched state. A sheet of this nature is able to follow the expansion of the pad as it absorbs fluid without the occurrence of any tension in the sheet, such tension otherwise striving to bend the pad. The flexibility and pliability of the pad is also enhanced by virtue of the general ability of the liquid-pervious sheet to follow the curved path of a pad applied to a knee wound for instance, simply by straightening out the folds or puckers.

In one preferred embodiment of the invention the wound pad is stretched to an extent that corresponds to its maximum expansion when taking up fluid.

The invention also relates to an absorbent dressing that includes an elastic and hydrophilic wound pad which expands when taking up fluid, and a liquid-impervious sheet fastened to that side of the wound pad that is intended to lie proximal from the wound when the dressing is used. The inventive dressing is characterized in that the liquid-impervious sheet includes a relatively large number of projections that are formed when the elastic wound pad, to which the liquid-impervious sheet is fastened after having expanded the wound pad mechanically in the plane of said sheet to a size that corresponds to the area of the sheet when flat, returns to a relaxed state. In one preferred embodiment, the area of the liquid-impervious sheet when flat corresponds to the area of the wound pad in an expanded state after maximum fluid absorption.

BRIEF DESCRIPTION OF THE DRAWINGS

The invention will now be described in detail with reference to the accompanying drawings, in which FIG. 1 is a schematic side view of apparatus for fastening plastic film to an elastic wound pad;

FIG. 2 shows the apparatus from above;

FIG. 3 is a sectional view taken on the line III—III in FIG. 2; and

FIG. 4 shows a wound pad that has been provided with a liquid-impervious sheet in accordance with one embodiment of the invention.

DETAILED DESCRIPTION OF THE INVENTION

The apparatus shown in FIGS. 1–3 includes four pairs of rolls 1–4 between which there is advanced a web 5 of plastic foam material, such as polyurethane foam for instance. A glue applying roller 6 is mounted downstream of the roll pair 2 and functions to apply glue to the by-passing web 5. Polyurethane film is then taken from a storage reel 8 and applied to the web 5, with the aid of a roller 9. The composite web then passes through the nip of the third roll pair 3. The long edges of the web 5 are held firmly by clamps 10 that run freely in fixed rails 11 on wheels 12, as evident from FIGS. 2 and 3. The rails 11 are mutually divergent between the roll pairs 1 and 2 and function to expand the web 5 laterally. The rolls of the roll pair 2 rotate at a higher speed than the rolls of the roll pair 1, so as to expand the web correspondingly in its longitudinal direction. Thus, the web 5 will have been stretched both transversally and longitudinally when reaching the roll pair 2. This stretched state is maintained at least until the web 5 leaves the roll pair 3. The plastic film 7 is thus applied and fastened to the web 5 whilst the web is in stretched state. The rails 11 are mutually convergent downstream of the roll pair 3 and the rolls of the roll pair 4 are driven at the same speed as the rolls of the roll pair 1, wherewith the web 5 will contract from its stretched state, both transversely and longitudinally, causing the film 7 to pucker and therewith reduce its transversal and longitudinal dimensions.

When the web 5 has passed the roll pair 4, wound pads that include a liquid-impervious sheet 7 are cut from the web 5, with the aid of means suitable to this end. The web is preferably held stretched until individual wound pads have been cut from the web. Alternatively, the web may be allowed to contract under its own elasticity, to the form that it had in its relaxed state or to the form that it obtains in the absence of any load thereon (a small degree of deformation may remain in the web when it relaxes from a stretched state) before cutting the individual wound pads therefrom.

FIG. 4 is a schematic perspective view of one such wound pad. This wound pad includes a piece 14 of absorbent foam material that has plastic film 15 fastened to its upper surface. The Figure shows the wound pad in a dry state, immediately after its manufacture. The wound pad has thus contracted to a relaxed state, meaning that its area has decreased in comparison with its area in its stretched state. The area of the film fastened to the upper side of the wound pad will, of course, have decreased to a corresponding extent.

Consequently, as the piece of foam 14 contracts elastically, a relatively large number of small projections will form in the film as the film puckers in following the reduction in area of the piece of foam 14. The plastic film will therewith become three-dimensional.

When the wound pad is in use, the foam 14 will absorb excessive fluid from the wound to which an absorbent pad that includes the wound pad has been applied. As the wound pad absorbs fluid, it will expand, or swell, both transversally and longitudinally and the area of the pad will increase at the rate at which fluid is absorbed. This increase in area is not counteracted by the film 15 in any way, and the film is able to follow the increase in area of the pad, by smoothing out the puckers or folds that form said projections. When the amount of fluid absorbed by the wound pad has reached an extent at which the pad has expanded so that its increase in area corresponds to the increase in area from a relaxed to a stretched state in the aforedescribed manufacture, the film 15 will have been smoothed out to a flat state. In the case of earlier known wound pads where the plastic film is applied to a piece of foam with said piece in a relaxed state, i.e. not stretched, the plastic film is unable to follow the increase in area of the piece of foam and the wound pad will strive to bend or arch as it absorbs fluid. Thus, because the plastic film is able to increase in area from a three-dimensional state to a flat state without the risk of tension forces occurring in the piece of foam 14, there is no danger of the edges of the foam 14 losing contact with the skin surrounding the wound onto which the wound pad 13 has been applied, solely as a result of the piece of foam absorbing fluid. In order to eliminate this risk completely, the extent to which the area of the piece of foam is increased when applying the plastic film during manufacture of the wound pad will correspond at least to the increase in area of the foam from a dry state to a saturated state.

In addition to eliminating the aforesaid risk, the described wound pad is more flexible than a similar wound pad provided with a flat plastic film, because the absorbent foam material 14 is able to curve with out requiring the plastic sheet to lengthen longitudinally and/or transversally through elastic deformation. When a dressing that includes an inventive wound pad is intended to be used in the treatment of knee wound or an elbow wound, it may therefore be suitable to give the plastic film in a flat state a larger area than what is motivated solely by expansion of the piece of foam in a saturated state, so that the flexibility of the foam can be utilized to a maximum.

The described dressing 13 can be held against a wound with the aid of some suitable fixation bandage, or may be affixed with the aid of an adhesive that will adhere to the skin but not to the bed of the wound.

Foam materials that swell when absorbing fluid may be used as an alternative to polyurethane foam. It is also conceivable to use other liquid-impervious materials as an alternative to plastic foams, such as nonwoven material for example, provided that these materials are sufficiently flexible to form said projections by folding or pleating as the absorbent material contracts from a stretched state to a relaxed state or non-loaded state.

The described wound pads may be sterile-packaged or otherwise.

It will be understood that the described embodiment can be modified without departing from the concept of the invention. For instance, the plastic film can be fastened to a stationary piece of extended or stretched foam material instead of to a moving web. The invention can also be applied with other absorbent materials, such as other elastic, pattern-cut or pleated-woven fabric included in surgical pads for instance. The elastic, absorbent material may also be stretched by other means than those described, prior to applying the liquid-impervious sheet. The invention is therefore restricted solely by the scope of the following claims.

We claim:

1. A method of fastening a liquid-impervious sheet to a wound pad that is comprised of an elastic, hydrophilic material and that will expand in all directions when absorbing fluid, the method comprising:

stretching the pad to a given extent in both a longitudinal and transverse direction of a longitudinal plane of the pad by applying a load to the pad so as to obtain a stretched pad;

fastening a flat liquid-impervious sheet to the stretched pad; and relieving the load acting on the pad thereby allowing the pad to contract, and cause the fastened liquid-impervious sheet to form a plurality of projections by puckering of the sheet.

2. The method according to claim 1, wherein the pad is stretched to an extent that corresponds to the extent to which the pad will have expanded with maximum absorption.

3. An absorbent dressing, which comprises:

an elastic and hydrophilic wound pad which expands when taking up fluid from a relaxed state to an expanded state; and a liquid-impervious sheet fastened to a side of the wound pad intended to lie proximal from the wound when the dressing is used, said liquid-impervious sheet comprising a) a plurality of projections when said pad is in the relaxed state, and b) a substantial planar configuration when said pad is in the expanded state.

4. The absorbent dressing according to claim 3, wherein the liquid-impervious sheet when flat has an area which corresponds to the area of the wound pad in the expanded state after maximum fluid absorption.

* * * * *